United States Patent
Schønfeldt (10) Patent No.: US 10,201,681 B2
(45) Date of Patent: *Feb. 12, 2019

(54) METHOD OF PREPARING A READY-TO-USE URINARY CATHETER AND A CATHETER ASSEMBLY FOR USE IN SAID METHOD

(71) Applicant: TELEFLEX LIFE SCIENCES UNLIMITED COMPANY, Athlone (IE)

(72) Inventor: Lars Schønfeldt, Helsingør (DK)

(73) Assignee: TELEFLEX LIFE SCIENCES UNLIMITED COMPANY, Co. Westmeath (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/840,571

(22) Filed: Dec. 13, 2017

(65) Prior Publication Data

US 2018/0099117 A1    Apr. 12, 2018

Related U.S. Application Data

(63) Continuation of application No. 14/438,589, filed as application No. PCT/DK2013/050342 on Oct. 25, 2013, now Pat. No. 9,872,970.

(30) Foreign Application Priority Data

Oct. 26, 2012    (DK) .................................. 2012 70662

(51) Int. Cl.
*A61M 25/00* (2006.01)
*B65B 5/04* (2006.01)
(Continued)

(52) U.S. Cl.
CPC ...... *A61M 25/002* (2013.01); *A61M 25/0017* (2013.01); *B65B 5/045* (2013.01);
(Continued)

(58) Field of Classification Search
CPC ........ A61M 25/002; A61M 2025/0062; A61M 25/0017; B65B 5/045; B65B 55/22; B65B 55/18
(Continued)

(56) References Cited

U.S. PATENT DOCUMENTS 4,863,016 A * 9/1989 Fong .................... A61M 25/002
206/210
5,178,282 A * 1/1993 Williams ............... A61B 50/30
206/363

(Continued)

FOREIGN PATENT DOCUMENTS

EP    0 923 398 B1    11/2001
EP    1 131 112 B1    2/2003
(Continued)

OTHER PUBLICATIONS

International Search Report and Written Opinion, Appl. No. PCT/DK2013/050342, dated Mar. 3, 2014.
(Continued)

*Primary Examiner* — Steven A. Reynolds
(74) *Attorney, Agent, or Firm* — Baker & Hostetler LLP (57) ABSTRACT

A method of preparing a ready-to-use catheter by providing a catheter assembly that has a first compartment that includes a catheter therein. The catheter includes on at least a part of its surface an exterior coating designed to reduce the coefficient of friction after treatment with a liquid swelling medium, and a second compartment containing a liquid swelling medium. The method includes sterilizing the catheter assembly, adding the liquid swelling medium to the first compartment for wetting/activating the exterior coating of the catheter, and storing the ready-to-use catheter. By using the method according to the invention, the sterilization of the catheter is effectuated in a dry-state, ensuring that the known problems with wet-sterilization are completely elimi-
(Continued)

nated and the need for preparing complicated and expensive liquid swelling mediums are no longer required.

19 Claims, 3 Drawing Sheets

(51) Int. Cl.
*B65B 51/00* (2006.01)
*B65B 55/18* (2006.01)
*B65B 55/22* (2006.01)

(52) U.S. Cl.
CPC ............. *B65B 51/00* (2013.01); *B65B 55/18* (2013.01); *B65B 55/22* (2013.01); *A61M 2207/00* (2013.01)

(58) Field of Classification Search
USPC .................... 206/570, 571, 210, 364, 363
See application file for complete search history.

(56) References Cited

U.S. PATENT DOCUMENTS

| | | |
|---|---|---|
| 2003/0055403 A1 | 3/2003 | Nestenborg et al. |
| 2003/0168365 A1 | 9/2003 | Kaem |
| 2005/0109648 A1 | 5/2005 | Kerzman et al. |
| 2006/0163097 A1 | 7/2006 | Murray et al. |
| 2006/0263404 A1* | 11/2006 | Nielsen ................. A61L 29/085 424/422 |
| 2007/0289887 A1* | 12/2007 | Murray ............... A61M 25/002 206/364 |
| 2008/0116106 A1 | 5/2008 | Lampropoulos et al. |
| 2008/0179208 A1 | 7/2008 | Murray et al. |
| 2009/0131917 A1 | 5/2009 | Kavanagh et al. |
| 2009/0200187 A1* | 8/2009 | Nestenborg ......... A61M 25/002 206/364 |
| 2010/0155268 A1 | 6/2010 | Murray et al. |
| 2010/0263327 A1 | 10/2010 | Murray et al. |
| 2010/0305527 A1 | 12/2010 | Murray et al. |
| 2011/0284409 A1 | 11/2011 | Murray et al. |
| 2012/0037525 A1 | 2/2012 | Peck et al. |
| 2012/0165790 A1 | 6/2012 | Gustaysson et al. |
| 2012/0228165 A1 | 9/2012 | Murray et al. |
| 2013/0146599 A1 | 6/2013 | Murray et al. |
| 2013/0153446 A1 | 6/2013 | Utas et al. |

FOREIGN PATENT DOCUMENTS

| | | |
|---|---|---|
| EP | 1 958 656 A1 | 8/2008 |
| EP | 2 060 296 A1 | 5/2009 |
| EP | 2 468 346 A1 | 6/2012 |
| EP | 2 545 952 A1 | 1/2013 |
| WO | 94/16747 A1 | 8/1994 |
| WO | 2004/075944 A2 | 9/2004 |
| WO | 2005/014055 A2 | 2/2005 |
| WO | 2007/146820 A2 | 12/2007 |

OTHER PUBLICATIONS

International Preliminary Report on Patentability, Appl. No. PCT/DK2013/050342, dated Feb. 16, 2015.
European Search Report, Appl. No. 17179057.9, dated Nov. 17, 2017.
U.S. Appl. No. 14/438,589, Restriction Requirement, dated Jul. 6, 2016.
U.S. Appl. No. 14/438,589, Non-Final Rejection, dated Nov. 7, 2016.
U.S. Appl. No. 14/438,589, Final Rejection, dated Feb. 17, 2017.
U.S. Appl. No. 14/438,589, Advisory Action, dated Apr. 19, 2017.
U.S. Appl. No. 14/438,589, Non-Final Rejection, dated May 31, 2017.
U.S. Appl. No. 14/438,589, Final Rejection, dated Sep. 1, 2017.
U.S. Appl. No. 14/438,589, Notice of Allowance, dated Sep. 28, 2017.

\* cited by examiner

METHOD OF PREPARING A READY-TO-USE URINARY CATHETER AND A CATHETER ASSEMBLY FOR USE IN SAID METHOD

CROSS-REFERENCE TO RELATED APPLICATIONS

This application is a division of U.S. patent application Ser. No. 14/438,589 filed Apr. 24, 2015, which is a 371 filing of International patent application no. PCT/DK2013/050342 filed Oct. 25, 2013, which claims priority to Danish patent application no. PA 2012 70662 filed Oct. 26, 2012, the entire content of each of which is incorporated herein by reference thereto.

BACKGROUND

The present invention relates to a method of preparing a ready-to-use catheter, a catheter assembly for use in said method, and a ready-to-use catheter obtained by said method.

Urinary catheters having exterior coatings have been known for many years. Typically the coating is a hydrophilic layer designed to reduce the coefficient of friction in the wet condition, so that the catheter may be inserted relatively painlessly into the urethra of the patient, and likewise removed therefrom when required.

In one type of catheters having exterior coatings the wetting fluid is initially kept separate from the hydrophilic surface, and released immediately prior to use, thereby activating the hydrophilic surface. In another type of such products, the wetting fluid is arranged in such a way that the hydrophilic surface is maintained constantly wetted, and thereby ready for immediate use.

Catherisation means greater risk for infection in the urinary tract, and the increase in multi-drug resistant organisms, combined with the well-documented costs of treating healthcare-associated infections, has led to a strong mandate to address and eliminate all potential avenues for infection. To reduce risk of infection, the urinary catheter as well as the wetting fluid needs to be sterilised. Furthermore, the surface of the urinary catheter should preferably remain uncontaminated prior to use.

Sterilisation of medical devices is typically performed at the time of manufacture, using techniques well known in the art such as beta-irradiation or fumigation with ethylene oxide gas.

However, sterilization of a wetted catheters e.g. an intermittent urinary catheter with a hydrophilic coating, is in general regarded cumbersome if not impossible, using the conventional techniques.

If gas, e.g. ethylene oxide, is used it must be allowed to have access to the catheter surface. However, the large volumes of wetting fluid surrounding the catheter will act as a barrier, preventing efficient penetration of ethylene oxide though the fluid. This means that the manufacturing process is made more complicated than would be desirable, requiring long and expensive periods of fumigation, and wet-sterilisation with fumigation is therefore generally regarded impossible.

Sterilisation using irradiation of coatings in the activated state, has the well-known problem that an undesirable cross-linking of said coating occurs, removing the coatings abilities to retain water. This has the consequence that the coefficient of friction increases undesirable when the catheter is stored in the wet, i.e. activated state.

One way of overcoming this problem is known from EP2303346, which discloses that by adding one or more buffers to the wetting fluids, it will be possible to prevent the pH-value of the activated hydrophilic coating dropping to levels that promote acid formation during wet sterilization and subsequent storage, thereby preventing ruining the coating on the catheters.

Another way of overcoming said disadvantages, is disclosed in EP1131112, describing that the water retention can increase dramatically and consequently the initial coefficient of friction be kept low, by carrying out wet-sterilisation of a medical device if the aqueous solution comprises hydrophilic polymers. According to EP1131112, wetting a hydrophilic coating with a polymer solution protects the above-mentioned properties during exposure to sterilisation using radiation.

However, for catheters which are sterilised wet, the coating of the catheter will either loos its water retention ability or obtain an undesirable increase in the coefficient of friction, unless specific compounds, such as buffers or polymers, are added to the wetting fluid, or unless other specific requirements are met, making the manufacturing process expensive and complicated.

Another problem is that the hydrophilic coatings of catheters, which are sterilised and stored wet, tend to lose their water retention abilities, resulting in increases in the coefficient of friction. Thus, the effective life of the catheters are limited or even over by the time the catheter is utilized.

The above problems are the main reason why catheters conventionally are sterilised in a dry condition, and why the wetting fluid is kept separate from the hydrophilic surface, and released immediately prior to use, as disclosed e.g. in EP0923398, EP1958656, US2003/0055403 and EP2545952.

The provision of the wetting fluid in a catheter assembly as disclosed in e.g. EP0923398 entails many advantages. For example, there is no need to find a water supply, and catheterisation can constantly be performed in any location and at any time. Further, the entire activation/wetting process can be performed under sterile conditions, without opening of the package.

However, a drawback with the catheters requiring activation/wetting immediately before use is that the methods of wetting are relatively complicated, making the wetting process tedious and difficult to perform by e.g. disabled users, such as tetraplegics or sclerosis patients having poor dexterity. Further, there is a significant risk that an inadequate wetting would occur from time to time, which would be both painful and potentially harmful for the user. Furthermore, in order to ensure a proper wetting, a substantial amount of wetting fluid is required, and in most products of this type, the wetting fluid in itself forms a substantial part of the overall weight of the product, making logistics more complicated and expensive.

In order to solve this problem, a vapour hydrated catheter assembly has been suggested in EP2060296. However, activation of the catheters coating using vapour, can result in inadequate wetting of the coating, which as discussed above will be both painful and harmful for the user. Furthermore, since only vapour is used for activating the catheter's coating in EP 2060296 the catheter assembly is a very complex construction and accordingly expensive to manufacture.

Thus, there is a requirement for providing a ready-to-use catheter in which the wetting fluid does not comprise expensive and complicated components in order to ensure that the coating can be maintained for a sustained period, where inadequate activation of the coating is prevented, and where the overall weight and size of the final catheter product is reduced more than hitherto known.

SUMMARY OF THE INVENTION

Therefore, it is a first aspect of the present invention to provide a ready-to-use catheter, which safely and effectively can be inserted into the urethra of the patient without causing discomfort.

It is a second aspect of the present invention to provide new ways of providing the sterilisation of a ready to use catheter to be carried out without detrimental effect to the water retention and the initial friction of the coating.

It is a third aspect of the present invention to provide a method for obtaining sterilized catheters without compromising the integrity of the sterilization.

It is a fourth aspect of the present invention to provide a ready-to-use catheter that allows for maximum shelf life of the catheter.

In a fifth aspect according to the present invention is provided a catheter that is inexpensive to manufacture and is simple and reliable to use.

In a sixth aspect according to the present invention is provided a catheter that are relatively small and easy to operate, especially by one hand.

The novel and unique features whereby these and further aspects are achieved according to the present invention is the fact the method for preparing a ready-to-use catheter, comprises providing a catheter assembly, comprising a first compartment comprising a catheter, said catheter comprises on at least a part of its surface an exterior coating arranged to reduce the coefficient of friction after treatment with a liquid swelling medium, and a second compartment comprising the liquid swelling medium, sterilising the catheter assembly, adding the liquid swelling medium to the first compartment for wetting the catheter's exterior coating, and storing the ready-to-use catheter.

First of all, by using the method according to the invention, the sterilisation of the catheter is effectuated in a dry-state before activation with liquid swelling medium, ensuring that the known problems with wet-sterilisation are completely eliminated and the need for preparing and controlling complicated and expensive liquid swelling mediums are no longer a requirement.

After sterilization of the catheter assembly the liquid swelling medium is added to the compartment containing the catheter under sterile/aseptic conditions by emptying the liquid content of the second compartment inside the sterile/aseptic boundaries of the catheter assembly. When the catheter's exterior coating comes into contact with the liquid swelling medium, said coating is activated, i.e. said coating swells to a smooth, slippery film making the catheter safe by reducing friction during insertion and withdrawal.

In the context of the present invention, "adding the liquid swelling medium", means that the swelling medium is added to the compartment in liquid form, i.e. that no phase change of the medium is required before the medium can be added. This not only provides a very simple embodiment, but also ensures that direct and sufficient contact of the liquid swelling medium with the entirety of the catheter's exterior coating is obtained, thereby preventing inadequate activation of the coating. In this respect it is preferred that when the liquid swelling medium is added to the first compartment, said medium has unobstructed access to the first compartment without any demands of physical phase changes e.g. liquid to vapour, in order to ensure a fast and efficient activation of the coating.

As the liquid swelling medium is added to the first compartment after the sterilisation is completed, but before the catheter is distributed to the end users, the activated low friction character of the coating will keep the catheter in a ready to use condition at all times. Furthermore, problems with inadequate wetting are eliminated, and the time-consuming and inconvenient method of wetting/activating the catheter immediately before use is no longer required for the user. This has the inherent advantage that no further preparation is required prior to use, so that the operation will be reduced to immediate withdrawal of the catheter from the first compartment, without the delay resulting from any required wetting period.

Within the context of the present invention the term "ready-to-use catheter" means a catheter in which the exterior coating designed to reduce the coefficient of friction has been treated with a liquid swelling medium, i.e. the coating is maintained constantly wetted and the catheter is therefore ready for immediate use.

Accordingly the catheter according to the present invention can be used directly by end users in any location, also outside the medical environment of a hospital or a clinic, as the requirement of access to a toilet and/or water is eliminated. Furthermore, since no further preparation is required prior to use the catheter is especially advantageously for e.g. by tetraplegic patients who often have a very poor dexterity, and therefore need a very simple insertion procedure.

During storage the first compartment not only acts as a cover ensuring that the surface of the urinary catheter remains uncontaminated prior to use, but said compartment can also functions as a protective sleeve enabling the user to hold the urinary catheter during catheterisation without it slipping due to the coating and without contaminating the sterilised surface.

It must be stressed, that the inventors surprisingly have discovered, that since the activation, i.e. addition of the swelling medium to the catheter, is effectuate, after the sterilisation is complete, the catheter can be stored without loosing its water retention ability and without obtaining an unadvantageous increase in the coefficient of friction.

In a preferred embodiment the method further comprises removing the second compartment from the catheter assembly after the liquid swelling medium has been added to the first compartment.

In order to ensure that the activated sterilised surface is not contaminated in this respect, it is preferred that the removal of the second compartment is effectuated by a method which does not compromise the sterility of the content of the first compartment.

In this respect, the second compartment can be removed from the catheter assembly using any conventional method as long as the first compartment containing the activated catheter is maintained sterile. In a preferred embodiment the second compartment is removed by e.g. die-cutting, welding and/or sealing e.g. by heat or glue, as said methods are both simple and inexpensive.

In a preferred embodiment the method according to the invention can further includes a process step for providing a hanger/strap in the catheter assembly or in proximity/adjacent to the first compartment. Said hanger/strap is intended for supporting handling of the catheter by suspending the package comprising the catheter on a wall, e.g. of a restroom. Fixation in hanging position could alternatively be provided by one or more sticky dot(s) mounted on the final package.

In addition or as an alternative, an easy-to-grip handle can be prepared in a final packaging comprising the activated catheter, e.g. in proximity to the first compartment. Said step(s) can e.g. be perform simultaneously with removing the second compartment, or in a separate step subsequent to removal of said second compartment.

The hanger/strap and/or easy-to-grip handle can in a preferred embodiment be prepared by reprocessing the second compartment, or alternatively be prepared in a part of the catheter assembly which does not contain the first or second compartment, e.g. in an intermediate section between said two compartments, or in a separate section placed in proximity to the first compartment, and is effectuated using e.g. dye cutting or similar methods.

Removing the second compartment before the catheter is placed in storage, not only means that the stored product will have a smaller size, but also that the liquid swelling medium present in the first compartment, will be lower than in e.g. the products where a separate dosage of liquid swelling medium is part of a stored catheter assembly, as e.g. known from EP0923398.

In the known products of this kind a substantial amount of wetting fluid is required in order to ensure a proper wetting, adding to the overall weight and size of the product.

In contrast, the method of the present invention provides the advantage, that any excess swelling medium, i.e. liquid swelling medium which is not used for activating the coating of the catheter, can be removed from the catheter assembly prior to storage, preferably simultaneously with or during the process of removing the second compartment from the catheter assembly.

Consequently, essentially all the swelling medium remaining in the first compartment after removal of the excess medium, is in this way used for its intended purpose, viz. has been assimilated by the coating, and the weight of the swelling medium in the final catheter packaging is therefore reduced to only slightly more than the wetting fluid contained in the coating when activated. The lower weight and size result in smaller packages, which makes the production easier and less costly, and also makes the products easier and less expensive to handle and store.

A further advantage of minimizing the amount of excess liquid swelling medium is that it avoids dripping from the tip of the catheter. Dripping is a known disadvantage of catheters stored wet.

In order to reduce the overall weight and size of the final product, the first compartment can in a first embodiment comprise a cavity, which very narrowly encloses the part of the catheter being provided with the coating. This results in a very lean and light product, where a very limited amount of water is sufficient to ensure an easy and highly effective activation of the entire coating. This also ensures, that excess amounts of liquid cannot spill from the package when the package is opened and thereby wet and/or stain the end user's clothing.

In a different embodiment excess liquid fluid medium and/or air surrounding the catheter can be removed by vacuum suction, preferably during removal of the second compartment. In this way a minimum weight of the product is obtained, as the only liquid remaining in the first compartment, is the liquid in the activated coating. Since air is also removed from the compartment, the size of the product can be reduced to a minimum and the fluid will be forced to be present only around the catheter, ensuring that smaller amounts of liquid swelling medium is required in order to activate the coating.

When a vacuum suction step is introduced in the method according to the invention, it is preferred that the first compartment is designed for not having any sharp edges which could damage the activated coating, or alternatively that the first compartment has a size and design which ensures that any sharp edges present in the first compartment are not brought into contact with the activated coating when the vacuum suction has been completed.

Vacuum can be provided on the first compartment in any convenient location using any conventional means, as long as the activated catheter is maintained sterile. In this respect it is preferred that the vacuum suction is applied to the catheter assembly during removal of the second compartment, e.g. by attaching the vacuum suction equipment to the second compartment, ensuring that any openings into the first compartment will be efficiently closed by e.g. welding and/or heat-sealing without providing any openings into the first compartment. It is in this respect preferred that the second compartment comprises e.g. a one-way valve which prevents the interior of the catheter assembly to be contaminated during attachment of the vacuum equipment. Said one-way valve can in a preferred embodiment be made of a gas diffusible material such as Tyvek®, which preferably also is incorporated into some embodiments of the catheter assembly when a gas-sterilisation is contemplated.

Since the sterilisation of the catheter assembly in the method according to the invention, is effectuated when the catheter is in its dry state, any conventional form for sterilisation can be used, as long as the integrity of the catheter is not compromised, e.g. by excessive heat or steam. It is important that all parts of the catheter assembly is sterilised, including the liquid swelling medium, in order to reduce risk of infection. The preferred sterilisation method includes, but is not limited to, the widely used industrial sterilizations technologies such as ethylene oxide, and γ- and β-irradiation. However, other methods can also be contemplated within the scope of the present invention, such as low-temperature hydrogen peroxide gas plasma, low-temperature peracetic acid gas plasma, vapour-phase hydrogen peroxide, ozone, chlorine dioxide, and high-intensity visible light.

In a simple and efficient method according to the invention ethylene oxide is a preferred method of sterilisation because of its undeniable advantages as an exceptional sterilizing agent having bactericidal, sporicidal, and virucidal activity. Ethylene Oxide sterilization is known in the art for sterilizing medical devices that cannot support conventional high temperature steam sterilization—such as devices that incorporate electronic components, plastic packaging or plastic containers. Said method is therefore well known in the art and will not be discussed in further details.

The liquid swelling medium can be added to the first compartment at any time before the catheter is placed in storage, however it is preferred that the swelling medium is added to compartment containing the catheter immediately after sterilization of the catheter assembly, i.e. when the catheter is still in the production facilities. In this way the activation process can be monitored and controlled, ensuring that an adequate activation/swelling of the catheter's coating is obtained.

A problem often encountered with the known coated catheters intended for activation immediately prior to use, is that the surface of the catheter can become sticky and adhere to the paper of the package causing the coating on the catheter to be damaged, destroyed or mutilated, resulting in inadequate wetting. When the swelling medium is added to the catheter immediately after sterilisation, as in the present invention, said problem is completely eliminated.

Within the context of the present invention, the term "immediately after sterilisation" means that the catheter assembly is still present in the production facilities and has not been relocated to a storage facility as finished goods for distribution to customers.

It is preferred that the liquid swelling medium is added to the first compartment as soon as possible after the sterilisation process is completed, and that said step is the next in the production line of the final catheter. However, a person skilled in the art will understand that if e.g. ethylene oxide sterilization is used, the catheter assembly need to go through a degassing phase to remove any particle of ethylene oxide from the first and second compartment, in order to prevent any undesirable by-products, e.g. the toxic ethylene glycol, when the liquid swelling medium is added to the first compartment. Such a degassing phase is accordingly not needed when the sterilisation is performed using radiation.

Thus, the term "immediately after sterilisation" means as soon as possible after the sterilisation step is completed and at a time when the liquid swelling medium can be added without any harmful side effects.

The present inventors have found that using the method according to the invention the activated sterilised ready-to-use catheter can be stored for a period exceeding the recommended shelf life time of the catheter which could be up to five years, typically 36 months, without detrimental effect to the activated coating, including the parameters of water retention and initial friction of the coating.

The present invention also relates to a catheter assembly comprising a first compartment comprising a catheter, said catheter comprises on at least a part of its surface an exterior coating arranged to reduce the coefficient of friction after treatment with a liquid swelling medium, and a second compartment comprising the liquid swelling medium, wherein the second compartment is made of a gas-permeable material.

Conventionally the compartments containing the liquid swelling medium is made of a gas-impermeable material, in order to prevent that any of the liquid can come into contact with the catheters coating for the whole lifetime of the catheter (typically 36 months). However, the inventors of the present invention have surprisingly found that a certain gas-permeability through the walls of said compartment is an advantage during the sterilization process thereby reducing process time and costs. Especially when an ethylene oxide process is used, the inventors has shown that the relatively small diffusion of gas from the second compartment to the first compartment will be sufficient to provide the desired humidity in the first compartment in order to ensure a very effective ethylene oxide sterilization process. However, said small diffusion is still so low that it will not affect the activation of the coating.

The term "gas-permeable" material should be understood in this context of the present invention to mean any material that will provide a liquid barrier before the liquid swelling medium is added to the first compartment, but will allow diffusion by evaporations of the actual liquid swelling medium.

In an especially advantageously embodiment the material can be chosen among relatively cheap materials such as polyethylene (PE) and polypropylene (PP), poly-ethylene-Vinyl-Acetate (EVA); and Poly-vinyl-chloride (PVC) thereby providing an inexpensive product.

Due to the relatively short duration the liquid swelling medium has to be present in the second compartment before it is added to the first compartment for activation of the coating, gas-impermeability of the second compartment is not demanded in the present invention since the loss of liquid swelling medium through a gas-permeable barrier will be negligible after a few days or weeks compared to duration of 36 months, and in the present invention said gas-permeability has even proven to be highly favourable.

Since the second compartment is gas-permeable this part is preferably either sealed of or removed from the remaining catheter assembly, e.g. by heat sealing or welding after sterilisation. Alternatively the entire catheter assembly can be wrapped in a gas-impermeable package in order to maintain stability of the product during the intended lifetime.

It is preferred that the gas-impermeable parts of the catheter assembly is sealed off from the gas-permeable parts during the removal of the second compartment, as described above.

When the catheter assembly is wrapped in an outer gas-impermeable packaging, and gas-sterilisation e.g. ethylene oxide sterilisation is contemplated, part of the outer packaging preferably comprises an intermediate section which consists of a gas diffusible bacteria barrier that allows for gas-sterilization, e.g. made of a Tyvek®-material or other paper based materials with similar properties, and arranged such that both the first and second compartment can be sterilised. If such a gas diffusible bacteria barrier is present this must later be sealed of or removed from the remaining catheter assembly, e.g. by heat sealing or welding as described above, in such a way that the activated catcher is stored in an gas impermeable packaging.

The first compartment can either be placed inside the outer packaging, be combined with said packaging or be formed directly in said packaging. In the latter embodiment, the first compartment is identical with a section of the outer packaging.

In a preferred embodiment according to the invention, the catheter assembly further comprises a collection bag arranged for collecting fluid e.g. urine during catheterisation. Said collection bag is preferably contained within or constitutes parts of the sterile boundaries of the outer packaging.

The collection bag is preferably not in liquid communication with the interior of the first compartment during storage, in order to ensure that liquid swelling medium will remain in close contact with the catheters coating. The opening between the collection bag and the first compartment is therefore preferably closed by a drainage closure. Said drainage closure is preferably a releasable closure, arranged such that a liquid communication path can be established between the first compartment and the collection bag without perturbation of the sterility of the catheter.

The drainage closure can be any kind of closure, which can be opened to drain fluid through the catheter to the collection bag during catheterisation. Said closure can e.g. be fixed folding of the packaging where the closure is opened by unfolding said folding, a peel welding activated by external forces, an external clamp closure or an internal plug that can be removed by external forces.

If the catheter packaging comprises a collection bag, it is preferred that when the catheter packaging is opened, the catheter can be trapped in the first compartment, allowing said compartment to function as a connecting hose between the catheter and collecting bag during catheterisation, allowing fluid, e.g. urine to flow into the collection bag through the catheter.

The packaging and/or catheter assembly can in a preferred embodiment be made of e.g. two sheets of film material that e.g. are welded together and comprising a welded joint. Such a welded joint may comprise a part provided as a peelable joint permitting separation of said sheets from each other for withdrawal of said catheter from the package.

Placing the catheter assembly into an outer packaging, is not only relevant if the first compartment is made of a gas-permeable material but also if said compartment is made of a soft and/or very flexible material which could rupture or brake and accordingly compromise the sterility of the first compartment when said material is subjected to handling during storage or transport.

It is preferred that the catheter assembly is arranged for easy opening and withdrawal of the catheter, and also that they are designed comprising an easy-to-grip handle that improves control during insertion and keeps fingers away from the sterile part of the catheter. It is advantageously if the packaging and/or catheter assembly in addition to maintaining the sterility, also is adapted to protecting the catheter, e.g. from sunlight, rough handling, or transportation. Packaging of this kind is also well known in the art.

One preferred example of a tear open system dedicated for users with low dexterity comprises tear marks placed in the lower part of the packaging/first compartment between to handgrips. The packaging can be forced open by forcing the two handgrips from each other, and the tip of the package can be used as a "none touch" to withdraw the catheter from the packaging.

In a preferred embodiment the second compartment comprises an outlet for discharging the liquid swelling medium into the first compartment, said outlet is closed by a releasable closure. Said closure can be any kind of closure which can be opened to expel the liquid swelling medium into the first compartment without compromising the sterility of the catheter assembly.

In one preferred embodiment said releasable closure is a rupturable closure in the form of a membrane or welding providing a relatively faint joint, which will be ruptured by applying pressure on the second compartment, thereby allowing the swelling medium to be in liquid communication with the interior of the first compartment.

In a different embodiment the second compartment can be compressible, having an outlet, which is arranged for being in fluid communication with an opening of the first compartment, when the releasable closure is released. The advantage of a compressible compartment is that all the liquid swelling medium easily can be forced into the first compartment, ensuring a sufficient activation of the coating. Thereby, the preparation of the catheter with the liquid swelling medium can be made very simple by application of a pressure to the walls of the compartment, whereby the liquid swelling medium will be transferred to the first compartment.

In a further embodiment the releasable closure is in the form of a rupturable membrane, connected with an operating device permitting rupturing of the membrane without opening the catheter package. Said operating device can e.g. comprise a rod-like member connected with the membrane and extending throughout the length of the second compartment and through an end wall of second compartment to a pulling member. When a pulling force is applied to said member, the membrane will rupture whereby the liquid swelling medium content in the second compartment will flow into the first compartment. In order not to compromise the sterility of the catheter assembly said rod-like member and pulling member is preferably contained within the outer walls of the catheter assembly.

In the above-mentioned embodiments the first compartment is not closed, only the second compartment is closed by the releasable closure, and when the releasable closure is opened the two compartments are in direct fluid communication. In a different embodiment the first compartment can also be closed by a releasable closure e.g. by placing an intermediate layer or membrane between the two compartments.

In a different embodiment the second compartment is made of a degradable material, which will dissolve within a few weeks, such that the liquid fluid medium automatically will be added to the first compartment after a time period. Said embodiment is especially advantageously when the sterilisation of the catheter assembly is performed using ethylene oxide, as this inherently will ensure that the degassing phase is completed before the coating is activated. Furthermore, since the liquid swelling medium automatically will be added to the first compartment, the catheter assembly can be directly placed in storage.

It is preferred that the first compartment comprises a cavity, which very narrowly encloses the part of the catheter being provided with the coating. This results in a very lean and light product, where a very limited amount of water is sufficient to ensure an easy and highly effective activation of the entire coating.

Within the context of the present invention the term "exterior coating" means any kind of layer placed on at least a part of the exterior of the catheter. In this respect it is not relevant if the coating is an outer adherent layer, a co-extruded layer, or a conventional coating, the only requirement is that the catheter comprises an outer layer designed to reduce the coefficient of friction in the activated condition.

In a preferred embodiment the coating is a hydrophilic coating, as these are well known in the art to reduce catheter-associated complications and to improve patient comfort and acceptance. These catheters are characterised by having a layer of polymer coating that is bound to the catheters surface. WO 94/16747 discloses a hydrophilic coating, which can be used in the present invention. Said coating improves retention of water on a surface, especially a surface of a medical device such as an intermittent urinary catheter, and is prepared by applying to the surface in one or more process steps at least one solution of components that will combine to form the hydrophilic coating. During the final step the surface is coated with an osmolality promoting agent, which is dissolved or emulsified in the solution or in the last solution to be applied when forming the hydrophilic coating. In order to maintain the low friction surface character during location of the catheter in the urethra and subsequent withdrawal therefrom and hereby reduce stinging pain it is further preferred to incorporate an osmolality promoting agent, such as NaCl, in the hydrophilic coating. The osmolality promoting layer disclosed in WO 94/16747 is optional regarding the present invention, as the liquid swelling medium can be saline water instead of tap water.

Hydrophilic coatings further have the advantage that the liquid swelling medium can be water or a saline solution i.e. a solution of 0.90% w/v of NaCl, or even higher concentrations in order to obtain hyper osmolality of the coating. The salt is preferred for being able to adjust the osmolality, and both water and saline are very inexpensive materials.

In any case it is preferred that the liquid swelling medium is not cytotoxic and complies with current health and safety regulations. In this respect it is desired that said swelling medium does not contain any hydrophilic polymers and/or any buffer components, in order to provide a simple and inexpensive liquid swelling medium, but also components which could have a harmful or negative impact on the user or the final product, should for obvious reasons be avoided.

In order to ensure that the activated, i.e. pre-lubricated and ready-to-use, catheter maintains it water retention and reduced friction force, it is advantageously that the first compartment is made of a gas-impermeable material, in order to prevent that the liquid which is contained in the activated coating, can evaporate during the lifetime of the catheter.

The term "gas impermeable" material should be understood in this context to mean any material that will be sufficiently tight against liquid losses caused by vapour diffusion from an compartment containing the activated coating for a period exceeding the recommended shelf life time of the catheter assembly, which could be up to five years, typically 36 months.

Said gas-impermeable material can be any suitable material, and can in a preferred embodiment be a gas impermeable thermoplastic film material such as a multiple layer film material comprising e.g. aluminium.

Since catherisation sometimes must be performed outside the users normal daily environment, e.g. in public toilets, where the general state of cleanliness cannot be expected to be of a sufficiently high standard, it is highly relevant that the ready-to-use catheter is placed in a first compartment/packaging which preferably is be designed for easy opening and withdrawal of the catheter.

The invention also relates to a ready-to-use catheter obtained by the method according to the present invention. Said catheter can be any kind of ready-to-use catheter including an intermittent catheter, an indwelling catheter, or a suprapubic catheter. Such catheters are all well known in the art and will not be discussed in further details in this application.

In some situations it may be preferred that several ready-to-use catheter packaging are combined in a single overall packaging, thereby resulting in lower weight and size which makes the products easier and less expensive to handle and store, not only from a manufacturing point of view but also for the intended end user. In such embodiments, it is preferred that a single second compartment contains sufficient liquid swelling medium in order to active several catheters placed in each their first compartment. Preferably the individual first compartments are mutually connected to each other via tear off lines. The swelling medium can e.g. be distributed via a manifold, which optionally can be removed from the first compartments together with the empty second compartment.

BRIEF DESCRIPTION OF THE DRAWINGS

The invention will be explained in greater detail below, describing only exemplary embodiments of the irrigation device with reference to the drawing, in which.

DETAILED DESCRIPTION OF THE INVENTION

The invention will be described below with the assumption that the exterior coating on the catheter is an intermittent catheter comprising a hydrophilic coating and that the liquid swelling medium is a saline solution. However, this assumption is not to be construed as limiting, and the catheter can just as easily be an indwelling catheter, or a suprapubic catheter, or a similar catheter.

Figure 1:
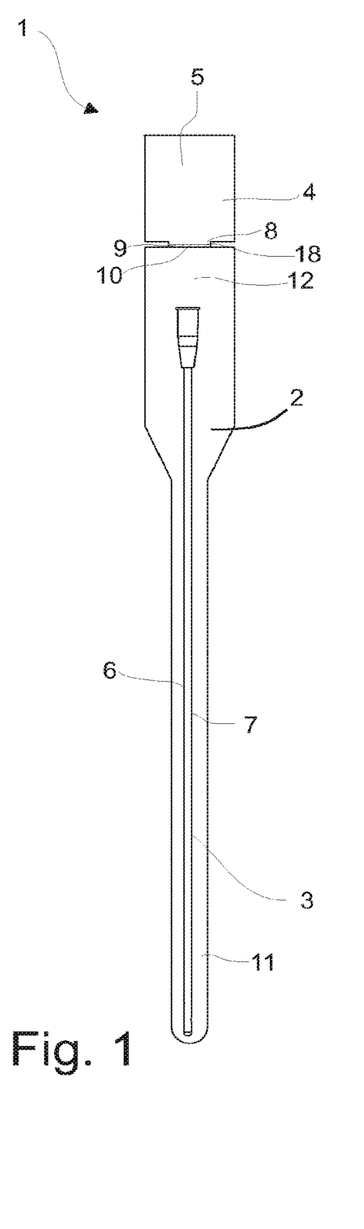
FIG. 1 shows a first embodiment of a catheter assembly according to the present invention.

FIG. 1 shows a first embodiment of a catheter assembly 1 according to the present invention. Said catheter assembly 1 consist basically of a first compartment 2 comprising the catheter 3, and a second compartment 4 comprising the liquid swelling medium 5, which in the present situation is a saline solution. Said catheter comprises on at least a part of its surface 6 an exterior hydrophilic coating 7 designed to reduce the coefficient of friction after treatment with the liquid swelling medium.

The second compartment 4 comprises an outlet 8 for discharging the liquid swelling medium into the first compartment, said outlet is closed by a releasable closure 9.

In the embodiment shown said releasable closure 9 is a membrane 18 providing a relatively faint joint, which will be ruptured by applying pressure on the second compartment 4, thereby allowing the liquid swelling medium 5 to be in liquid communication with the interior of the first compartment 2 though an opening 10 in said compartment. However, within the scope of the present invention said closure can be any kind of closure which can be opened to expel the liquid swelling medium into the first compartment without compromising the sterility of the catheter assembly.

The first compartment 2 comprises a cavity 11, which very narrowly encloses the part of the catheter 3 being provided with the hydrophilic coating. This results in a very lean and light product, where a very limited amount of liquid swelling medium is sufficient to ensure an easy and highly effective activation of the entire coating.

In the embodiment shown the first compartment 2 is made of a gas-impermeable material and the second compartment 4 is made of a gas-permeable material. It is preferred that the gas-permeable parts of the catheter assembly i.e. the second compartment 4, is removed and/or sealed off from the first compartment 2 in order to maintain sterility of the ready-to-use catheter during the intended lifetime. This is preferably obtained by applying a seal (not shown) in an upper part 12 of the first compartment 2, i.e. the part that is not containing the catheter.

Figure 2:
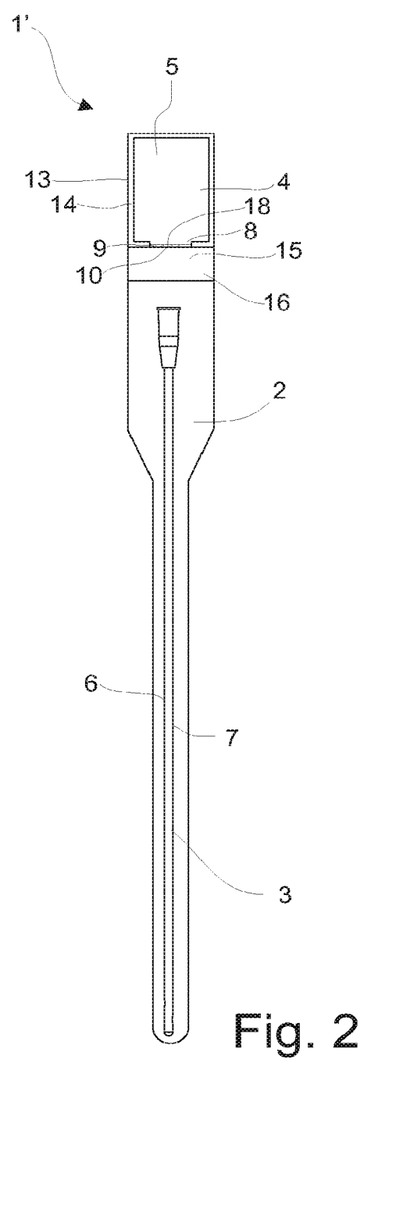
FIG. 2 shows a second embodiment of a catheter assembly according to the present invention.

FIG. 2 shows a second embodiment 1' of the catheter assembly according to the present invention. In said embodiment the catheter assembly 1 in FIG. 1 has been placed in an outer packaging 13. Said packaging 13 is arranged such that the first compartment 2 is part of said packaging, and the second compartment is placed inside the packaging. A gap 14 is provided between the second compartment 4 and the packaging 13.

The second compartment 4 has been made of a gas-permeable material. The packaging 13, which constitutes the sterile boundaries, is in contrast made of a gas-impermeable material in order to prevent that the liquid in the activated coating evaporates during the shelf life time of the catheter. This will not only ensure that the liquid, which is contained in the activated coating, cannot evaporate during the lifetime of the catheter, but also that any gas evaporating from the second compartment 4, before the sterilisation step and before the liquid medium is added to the first compartment, will be directed to the gap 14 allowing said gas to diffuse to the first compartment 2, and into the interior of the first compartment 2. This will advantageously ensure that the humidity obtained thereby in the first compartment 2 provides a very effective ethylene oxide sterilization process. The diffusion of gas from the second compartment to the first compartment will be sufficient to provide the desired humidity in the first compartment in order to ensure a very effective ethylene oxide sterilization process, but still to low to activate the coating.

A section 15 of the packaging 13 consists of a gas diffusible bacteria barrier 16 e.g. made of Tyvek® that allows for gas-sterilization.

Figure 3:
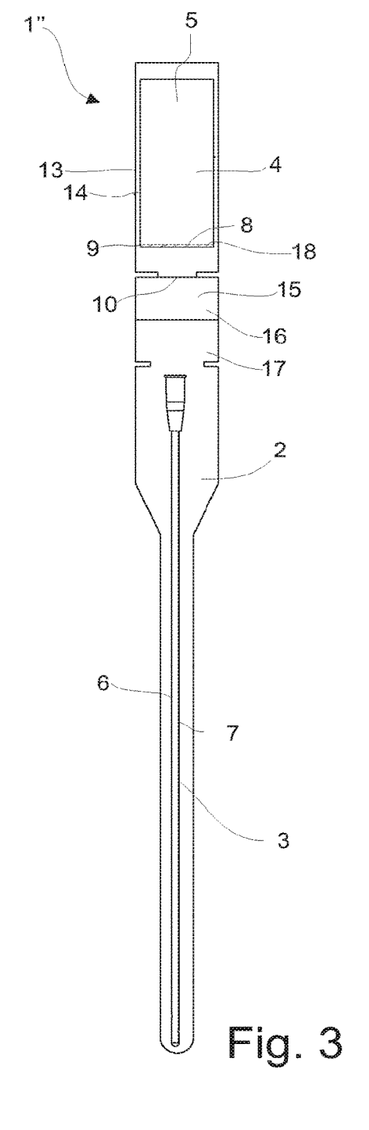
FIG. 3 shows a third embodiment of a catheter assembly according to the present invention.

FIG. 3 shows a third embodiment 1" of the catheter assembly according to the present invention. Said embodiment corresponds basically to the catheter assembly 1' in FIG. 2. i.e., the second compartment 4 is placed inside an upper part of the packaging 13. As for the other embodiments 1,1' the second compartment also comprises a membrane 18 which will be ruptured by applying pressure on the second compartment 4, thereby allowing the liquid swelling medium 5 to be in liquid communication with the interior of the first compartment 2.

The embodiment in FIG. 3 however has the addition that it comprises an intermediate section 17, adapted for easy removal and/or sealing of the first compartment 2.

The catheter assembly 1,1' and 1" can be prepared by any conventional means, and have any form or design. In the embodiments shown the second compartment 4 is placed at the upper end of the catheter assembly, however the second compartment 4 could equally well be placed in the opposite end or be placed on one or more sides of the first compartment 2. The only requirement is that during the sterilisation of the catheter assembly 1,1',1" the catheter 3 is contained in the first compartment 2, whereas the liquid swelling medium is contained in the second compartment 4, and that the two compartments are not in liquid communication with each other.

Since the sterilisation is effectuated in the catheter's dry state, the known problems with wet-sterilisation are completely eliminated and the need for preparing and controlling complicated and expensive liquid swelling mediums are no longer a requirement.

After sterilization of the catheter assembly 1,1',1" the liquid swelling medium 5 can conveniently be added to the first compartment 2 under sterile/aseptic conditions by rupturing the membrane 18, by applying force to the second compartment 4. This will ensure that the hydrophilic coating 7 comes into contact with the liquid swelling medium 5, whereby said coating is activated, i.e. said coating 7 swells to a smooth, slippery film 20 making the catheter 3 safe in use by reducing friction during insertion and withdrawal. Since the activation, i.e. addition of the swelling medium to the catheter is effectuate after the sterilisation is complete, the catheter 3 can be stored without loosing its water retention ability and accordingly without obtaining an unadvantageous increase in the coefficient of friction.

Since no further preparation is required prior to use, all the user has to do it to withdraw the catheter 3 from the first compartment 2. Accordingly the catheter according to the present invention can be used directly by end users in any location, e.g. by tetraplegic patients.

During storage the first compartment 2 or the packaging 13 not only acts as a cover ensuring that the surface 6 of the catheter 3 remains uncontaminated prior to use, but said cover can also functions as a protective sleeve enabling the user to hold the urinary catheter during intermittent catheterisation without it slipping due to the coating and without contaminating the sterilised surface.

Any gas-permeable parts of the catheter assembly according to the invention, must preferably be removed and/or sealed off from the remaining catheter assembly, in order to maintain stability of the catheter during the intended lifetime.

This can e.g. be effectuated at the same time as the second compartment 4 is removed from the catheter assembly 1,1',1". It is preferred that the second compartment 4 is removed by e.g. welding and/or heat-sealing, as said methods are both simple and inexpensive and at the same time will ensure that the first compartment 2 effectively is sealed off.

Figure 4:
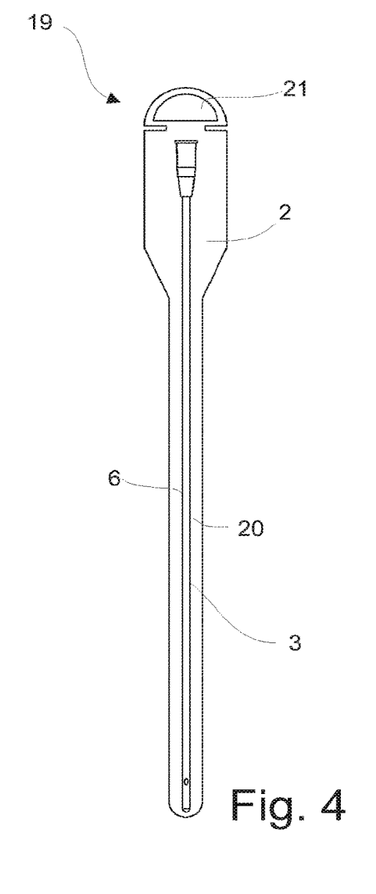
FIG. 4 shows a final package of the third embodiment according to the invention, wherein the second compartment has been removed.

In FIG. 4 is shown final package 19 according to the invention where the second compartment has been removed. Said package include the activated catheter 3', i.e. the coating 7 has been activated to provide a smooth, slippery film 20.

During the removal of the second compartment a hanger/strap 21 placed in proximity to the first compartment as been provided. Said hanger/strap is intended for supporting handling of the catheter by suspending the packaging 13 on a wall, e.g. of a restroom. The hanger/strap is prepared in an intermediate section 17 of the catheter assembly, i.e. a section that neither contains the first 2 or second compartment 4, nor the gas diffusible bacteria barrier 16.

Removing the second compartment before the catheter package 19 is placed in storage, not only means that the stored catheter package 19 will have a smaller size, but also that the liquid swelling medium present in the first compartment has been used for its intended purpose and is contained in the hydrophilic coating. The weight of the swelling medium in the final catheter package is therefore reduced to only slightly more than the wetting fluid contained in the coating when activated, also eliminating the known problems that dripping from the tip of the catheter is avoided. The lower weight and size result in smaller packages, which makes the production easier and less costly, and also makes the products easier and less expensive to handle and store.

Figure 5:
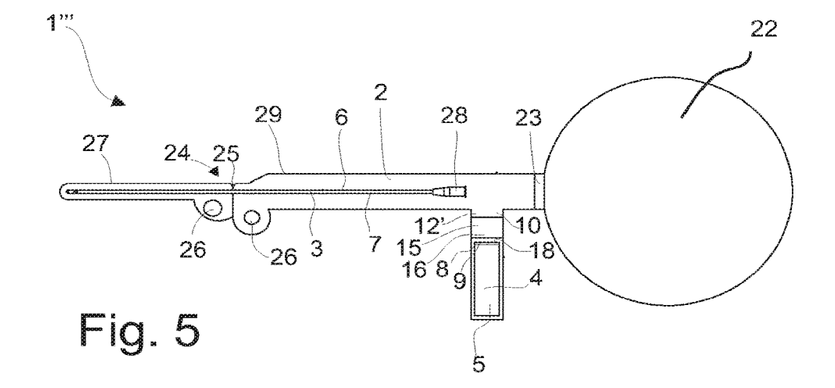
FIG. 5 illustrates a fourth embodiment of a catheter assembly according to the present invention.

FIG. 5 illustrates a fourth embodiment of the catheter assembly 1'" according to the invention. For like part the same reference numbers are used as for the previous embodiments.

In the present embodiment the second compartment 4, is not an extension of the first compartment 2, but is instead placed as a projection, extending perpendicular to the first compartment 2. Said second compartment has in FIG. 6 been removed as described above, by applying a seal (not shown) in a section 12' of the first compartment 2.

In addition to encasing the first and second compartment, the outer packaging 13 further contains within its sterile boundaries, a collection bag 22 arranged for collecting urine during catheterisation.

The collection bag 22 is preferably not in liquid communication with the interior of the first compartment 2 during storage, in order to ensure that liquid swelling medium 5 which is not bound to the exterior coating 7 will flow into the collection bag 22.

The opening between the collection bag 22 and the first compartment 2 is closed by a drainage closure 23. Said drainage closure is a releasable closure, arranged such that a liquid communication path can be established between the first compartment 2 and the collection bag 22 without perturbation of the sterility of the catheter packaging.

Figure 6:
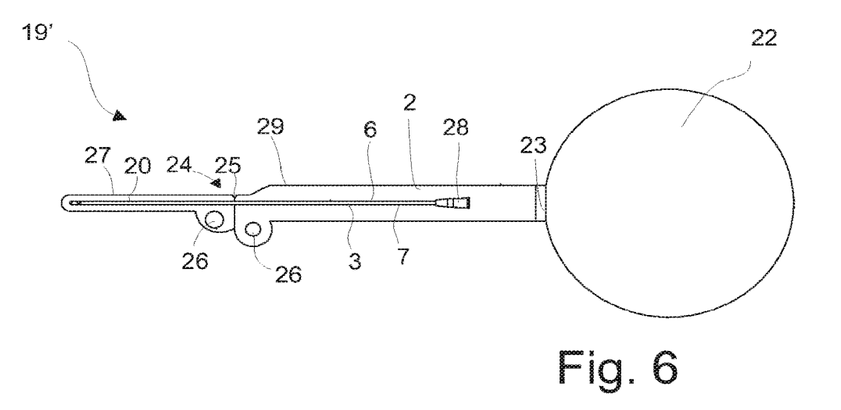
FIG. 6 shows a final package of the fourth embodiment according to the invention, wherein the second compartment has been removed.

An example of a tear open system 24 dedicated for users with low dexterity is shown in FIGS. 5 and 6 where tear marks 25 are placed between to handgrips 26. When the package is forced open by forcing the two handgrips from each other, the tip of the package 27 is used as a "none touch" to withdraw the catheter 6 from the primary package 13 until the catheters connector 28 is trapped in the first compartment 2 just before the tear marks 25. The part 29 of the first compartment 2, which is connected to the collection bag 22, then functions as a kind of connecting hose between catheter 6 and collecting bag 22 during catheterisation, allowing urine to flow through the catheter into the collection bag thereby providing a very hygienic system, which can be used at any location. After catheterisation the catheter 6 can by dropped back in the collecting back 22 and a knot can be tied on the packaging 13 thereby closing the system, which is now ready to be thrown away.

The ready-to-use catheter according to the invention has a simple and inexpensive design, and can therefore be used equally well for both privately and in medical or hospital facilities where known catheters are too troublesome and complicated to use.

Modifications and combinations of the above principles and designs are foreseen within the scope of the present invention.

What is claimed is:

1. A method of preparing a ready-to-use catheter, said method comprising:
    providing a catheter assembly, comprising
    i. a first compartment comprising a catheter, said catheter comprises on at least a part of its surface an exterior coating arranged to reduce the coefficient of friction after treatment with a liquid swelling medium, and
    ii. a second compartment comprising the liquid swelling medium,
    wherein the first and second compartments are configured to allow the liquid swelling medium to flow from the second compartment and be received in the first compartment, and wherein said catheter assembly is packaged by being wrapped or placed in a gas-impermeable package,
    said method comprising the additional steps of:
    sterilising the catheter assembly, including the first and second compartments, catheter and liquid swelling medium,
    transferring the liquid swelling medium, in a liquid state, from the second compartment to the first compartment under sterile conditions by emptying the sterilized liquid content of the second compartment inside the sterile boundaries of the catheter assembly and into the first compartment for contact with the catheter and for wetting/activating the catheter's exterior coating, wherein said liquid swelling medium is added to the first compartment when the catheter assembly is in the production facilities, and
    storing the ready-to-use catheter until needed for use.

2. A method according to claim 1, wherein the sterilization of the catheter assembly is performed by γ- or β-irradiation.

3. A method according to claim 1, wherein the liquid swelling medium is added to the first compartment immediately after sterilization of the catheter assembly.

4. A method according to claim 1, wherein the ready-to-use catheter can be stored for a period of at least 36 months.

5. A method according to claim 1, wherein the method further includes a step for removing any excess liquid swelling medium and/or air present in the first compartment after the catheter exterior coating has been wetted/activated.

6. The method of claim 1, which comprises forming as an intermediate product, a sterilized catheter assembly comprising the first compartment containing the catheter that has on at least a part of its surface an exterior coating that can provide a reduced coefficient of friction when contacted with a liquid swelling medium, and the second compartment containing the liquid swelling medium, wherein the catheter assembly is sterilized with the first compartment in a dry state prior to contact of the catheter exterior coating with the liquid swelling medium.

7. The method of claim 1, wherein the ready-to-use catheter is wrapped or placed in a gas-impermeable package.

8. The method of claim 1, wherein the second compartment of the catheter assembly comprises an outlet for discharging the liquid swelling medium, said outlet is closed by a releasable closure and the outlet is arranged for being in fluid communicating with an opening of the first compartment, when the releasable closure is released.

9. The method of claim 8, wherein the releasable closure is a rupturable closure.

10. The method of claim 9, wherein the rupturable closure is in the form of a membrane or welding, providing a relatively faint joint, which is ruptured by applying pressure on the second compartment.

11. The method of claim 10, wherein the rupturable membrane is connected with an operating device arranged for rupturing the membrane without opening the catheter package.

12. The method of claim 6, wherein the second compartment of the intermediate product is a compressible compartment.

13. The method of claim 6, wherein the sterilized catheter assembly comprises a packaging for accommodating the catheter assembly, said packaging is made of a gas-impermeable material.

14. The method of claim 13, wherein the first compartment is placed inside the packaging, is combined with said packaging or is formed directly in the packaging.

15. The method of claim 13, wherein said packaging comprises a gas diffusible bacteria barrier that allows for gas-sterilization.

16. The method of claim 6, wherein the first compartment comprises a cavity which very narrowly encloses the part of the catheter that has the exterior coating.

17. The method of claim 6, wherein the exterior coating of the catheter is a hydrophilic coating.

18. The method of claim 6, wherein the liquid swelling medium does not contain any hydrophilic polymers and/or any buffer components.

19. The method of claim 6, wherein a single second compartment is connected to at least two first compartments.

* * * * *